United States Patent [19]

Winchell et al.

[11] Patent Number: 5,061,243
[45] Date of Patent: Oct. 29, 1991

[54] SYSTEM AND APPARATUS FOR THE PATIENT-CONTROLLED DELIVERY OF A BENEFICIAL AGENT, AND SET THEREFOR

[75] Inventors: David A. Winchell, Spring Grove; Thomas A. Fowles, McHenry; Richard Mitchell, Lindenhurst, all of Ill.

[73] Assignee: Baxter International Inc., Deerfield, Ill.

[21] Appl. No.: 308,972

[22] Filed: Feb. 8, 1989

Related U.S. Application Data

[63] Continuation of Ser. No. 171,238, Mar. 16, 1988, abandoned, which is a continuation of Ser. No. 65,697, Jun. 16, 1987, abandoned, which is a continuation of Ser. No. 762,985, Aug. 6, 1985, abandoned.

[51] Int. Cl.⁵ .............................................. A61M 5/00
[52] U.S. Cl. .................................... 604/132; 604/153; 604/185; 604/246
[58] Field of Search ............ 604/93, 132, 185, 891.1, 604/892.1, 153, 246

[56] References Cited

U.S. PATENT DOCUMENTS

| | | |
|---|---|---|
| 2,471,623 | 5/1969 | Hubbell ............................ 604/185 X |
| 2,907,325 | 10/1959 | Burke ............................... 604/185 |
| 3,039,399 | 6/1962 | Everett ........................... 604/153 X |
| 3,469,578 | 9/1969 | Bierman .......................... 604/132 |
| 3,469,578 | 9/1969 | Bierman .......................... 604/132 |
| 3,486,539 | 12/1969 | Jacuzzi ............................ 141/329 |
| 3,527,220 | 9/1970 | Summers ......................... 128/260 |
| 3,895,631 | 7/1975 | Buckles et al. ................. 604/132 |
| 4,013,074 | 3/1977 | Siposs .............................. 604/891 |
| 4,121,584 | 10/1978 | Turner et al. .................... 604/246 |
| 4,215,689 | 8/1980 | Akiyama et al. ................. 128/214 |
| 4,273,121 | 6/1981 | Jassawalla ....................... 128/214 F |
| 4,349,133 | 9/1982 | Christine ......................... 222/183 |
| 4,386,929 | 6/1983 | Peery et al. ..................... 604/132 |
| 4,394,938 | 7/1983 | Frassanito ........................ 222/207 |
| 4,447,232 | 5/1984 | Sealfon et al. ................... 604/134 |
| 4,456,009 | 6/1984 | Vcelka et al. .................... 604/152 |
| 4,544,371 | 10/1985 | Dormandy et al. .......... 604/185 X |
| 4,548,607 | 10/1985 | Harris .............................. 604/891 |
| 4,551,133 | 11/1985 | DeBeyl et al. .................... 604/66 |
| 4,559,038 | 12/1985 | Berg et al. ....................... 604/153 |
| 4,565,542 | 1/1986 | Berg ................................. 604/131 |
| 4,588,394 | 5/1986 | Schulte ................................ 604/9 |
| 4,601,707 | 7/1986 | Albisser et al. ................. 604/131 |
| 4,634,427 | 1/1987 | Hannula et al. ............. 604/185 X |
| 4,668,231 | 5/1987 | DeVries et al. .................. 604/891 |
| 4,699,615 | 10/1987 | Fischell .......................... 604/131 |

FOREIGN PATENT DOCUMENTS 0168675  1/1986  European Pat. Off. .

OTHER PUBLICATIONS

"Postoperative Demand Analgesia", Michael Keeri-Szanto, M.D. et al., Surgery, Gynecology & Obstetrics, Apr. 1972, vol. 134, pp. 647-651.

"Patient-Controlled Analgesic Therapy: Clinical Experience", A. Tamsen et al., Acta Anaesthesiol. Scand. Suppl., 1982, vol. 74, pp. 157-160.

(List continued on next page.)

*Primary Examiner*—C. Fred Rosenbaum
*Assistant Examiner*—Corrine Maglione
*Attorney, Agent, or Firm*—Paul E. Schaafsma; Amy L. H. Rockwell; Paul C. Flattery

[57] ABSTRACT

An apparatus (60) and system (20) are disclosed for the patient-controlled delivery of an analgesic or other beneficial agent 142, while preventing administration of a toxic quantity of the beneficial agent. The invention permits delivery of fractional doses to a patient in quantities which are directly proportional to the time period since the last dose or fraction thereof was delivered to the patient. In the preferred embodiments the apparatus includes a housing (58) including a casing (88) and a back plate (86), the housing containing a control switch (84) for opening and closing downstream conduit (62) and for depressing a floating plate (100) that thereby compresses a dose reservoir (90) with the beneficial agent (142) therein. A spring (124) biases the control switch (84).

30 Claims, 5 Drawing Sheets

OTHER PUBLICATIONS

"Multiple and Single-Dose Kinetics of Morphine in Patients with Post-operative Pain": B. Dahlstrom et al., Acta Anaesthesiol. Scand. Suppl., 1982, vol. 74, pp. 44-46.

"Self-administration of Intravenous Analgesics", William H. Forrest, Jr., et al., Anesthesiology, vol. 33, No. 3, pp. 363-365, Sep. 1970.

"Patient Contolled Analgesia", Richard L. Bennett, M.D. and Ward O. Griffen, M.D., six pages, source unknown.

"Demand Analgesia", M. Keeri-Szanto, M.D., F.R.C.P.(C) from International Symposium on Intravenous Anesthesia, 1st, 1979 Denver.
Trends in Intravenous Anesthesia, editors, J. A. Aldrete and T.H. Stanley; Miami: Symposia Specialists, 1980. pp. 417-429.

"Patient-controlled Analgesic Therapy, Part III", A Tamsen et al., Clin Pharmacokinet vol. 7, pp. 252-265, 1982.

"-controlled Analgesic Therapy, Part IV", B. Dahlstrom et al., Clin Pharmacokinet, vol. 7, pp. 266-279, 1982.

"Postoperative Demand for Analgesics in Relation to Individual Levels of Endorphins and Substance P in Cerebrospinal Fluid", A. Tamsen et al., Pain, vol. 13, pp 171-183, 1982.

"Obstetric Analgesia", James S. Scott, M. D., Amer. J. Obstet. Gynec., vol. 106, No. 7, Apr. 1, 1970, pp. 959-978.

"Patient-controlled Analgesic Therapy, Part 1", A. Tamsen et al., Clin Pharmacokinet vol. 7, pp. 149-163, 1982.

"Patient-controlled Analgesic Therapy, Part II", A. Tamsen et al., Clin. Pharmacokinet vol. 7, pp. 164-175, 1982.

"Comparison of Buprenorphine and Pethidine Given Intravenously on Demand to Relieve Postoperative Pain", K. Chakravarty et al., from British Medical Journal, 1979, vol. 2, pp. 895-897.

"Control of Postoperative Pain by Interactive Demand Analgesia", C. J. Hull et al., British Journal of Anaesthesia (1981), vol. 53, pp. 385-391.

"Patient Administration of IV Buprenorphine for Postoperative Pain Relief Using the 'Cardiff' Demand Analgesia Apparatus", J. M. Gibbs et al., British Journal of Anaesthesia, vol. 54, pp. 279-283, 1982.

"Comparison of Meptazinol and Pethidine Given IV on Demand in the Management of Postoperative Pain", P. J. Slattery et al., Br. J. Anaesthesiol. vol. 53(9), pp. 927-930, 1981.

"Postoperative Pain Relief", B. Kay; Anesthesia vol. 36, pp. 949-951, 1981.

"Studies in Pain with the Analgesic-Demand System" from Anesthesia and Analgesia . . . Current Researches, P. Sechzer, M.D., vol. 50, No. 1, Jan.-Feb., 1971, pp. 1-10.

"Patient-Controlled Analgesia", from Annals of Surgery, vol. 195, No. 6, Jun. 1982, pp. 700-705.

"Variation in Postoperative Analgesic Requirements in the Morbidly Obese Following Gastric Bypass Surgery", Richard Bennett, M.D., et al. from Pharmacotherapy, vol. 2, No. 1, Jan.-Feb. 1982, pp. 50-53.

"Patient Controlled Analgesic Therapy in the Early Postoperative Period", A. Tamsen et al., Acta Anaesthesiol. Scand. 1979, vol. 23(5), pp. 462-470.

"Results are Better When Patients Control Their Own Analgesia", JAMA Medical News, Feb. 19, 1982, vol. 247, No. 7, pp. 945-947.

"Patient-Controlled Analgesia", David A. Graves et al., Annals of Internal Medicine 1983, vol. 99, pp. 360-366.

"Morphine Titration in Postoperative Laparotomy Patients Using Patient-Controlled Analgesia", Richard Bennett, M.D. et al., Current Therapeutic Research, vol. 32, No. 1, July 1982, pp. 45-52.

SYSTEM AND APPARATUS FOR THE PATIENT-CONTROLLED DELIVERY OF A BENEFICIAL AGENT, AND SET THEREFOR

This application is a continuation of application Ser. No. 171,238, filed Mar. 16, 1988, now abandoned, which is a Continuation of application Ser. No. 65,697, filed June 16, 1987, now abandoned, which is a Continuation of application Ser. No. 762,985filed Aug. 6, 1985, now abandoned.

TECHNICAL FIELD OF THE INVENTION

The present invention is directed to the controlled delivery of preselected quantities of fluid and is more particularly directed to a system and apparatus for the delivery of a preselected quantity of drug or other beneficial agent to a patient, wherein the patient can control, up to the maximum preselected amount, the amount of beneficial agent administered.

BACKGROUND OF THE INVENTION

Analgesics comprise a large portion of the drugs administered by hospital pharmacies. Analgesics are often prescribed postoperatively to relieve pain. There is great difficulty in properly administering analgesics. The patient need for analgesics varies greatly. Some patients continue to suffer even after given conventional doses of analgesics. Similarly, some patients never request analgesics. Age, hypatic function, renal function, and other medication all affect the pharmacokinetics of analgesics.

Due to the fear of addiction with narcotic drugs, doctors tend to underprescribe the use of analgesics. For the same reason, nurses tend to underadminister analgesics.

In the area of analgesics, there has been much activity in the last several years directed to letting the patient control how much drug he or she receives. It has been found that as a group, patients controlling the quantity of pain killer they receive use less than patients who must request the administration of a pain killer. Apparently, one factor is the psychological relief present when a patient knows he or she is in control of the amount of drug to be received, up to a maximum limit.

The inventors are aware of certain devices that are on the market, or that are in the process of obtaining government regulatory approval, which are directed to the patient-controlled delivery of analgesics. These devices include the Cardiff Palliator by Pye Dynamics Ltd. or Graseby Dynamics of the United Kingdom; the On-Demand Analgesic Computer (ODAC) model JSI 0299 made by Janssen Scientific Instruments; a PCA infuser by Abbott Laboratories, Inc.; the Harvard PCA Pump by C. R. Bard Inc.; and a pump by Deltec Systems Inc. All of these pumps are large and bulky, the smallest pump being the Deltec pump, which is approximately as large as a telephone. All of the above-mentioned devices are electromechanical in nature, requiring a separate power source. Although the Deltec unit may conceivably be worn by patients, it is believed that the remainder of the pumps mentioned above confine the patient to a bed, or some other fixed location.

Another problem associated with these devices is that after the drug is loaded into the pump, certain control factors must be set by the nurse or other person who actually sets up the pump with the patient. These limits may include the minimum time period for delivering a dose of the drug and the size of the drug dose to be delivered when the patient actuates the pump. These limits to be set by the nurse or other personnel provide extra opportunities for error in administering the pain killer and provide additional sources of concern for hospital personnel that must be checked and rechecked during administration of the drug. Yet another problem with existing devices is that they are relatively expensive and may include some rather complex electronic components.

It would be desirable for the medical community to have an apparatus and system for the patient-controlled delivery of a pain killer or other beneficial agent which does not have any of the problems identified above and which can be made at a cost low enough to permit the entire apparatus and system to be disposable, if desired.

SUMMARY OF THE INVENTION

The apparatus and system of the present invention provide for the patient-controlled delivery of a analgesic or other beneficial agent up to a maximum, safe rate limit, while avoiding all of the problems described above. The apparatus is small and lightweight, permitting the patient to be ambulatory. In the preferred embodiment, the apparatus is the size of a large men's wristwatch and may be worn in the same manner as a watch, about the wrist.

The apparatus is completely mechanical, requiring no electrical power source of any kind which could otherwise malfunction. There is no concern about a battery or battery power level or battery life. No expensive controls, either computer operated or otherwise are required. The apparatus is completely preset by the manufacturer, so that once the proper drug is loaded into the system, no further setting of any administration limits, such as dose quantity or the dose delivery time period, are either necessary or possible.

The apparatus of the invention provides a certain maximum volume of beneficial agent that may be delivered in a certain time period. The apparatus permits the delivery to the patient, as controlled by the patient, of a bolus amount of beneficial agent in discrete dose volumes or fractional dose volumes, as selected by the patient; however, the apparatus assures that the fractional bolus doses which the patient may decide to administer will be of a size increasing substantially linearly with the time interval since administration of the last full bolus dose or fractional bolus dose, thereby preventing a drug overdose.

The apparatus and system of the present invention are inexpensive enough relative to hospital labor costs so that the entire apparatus and system may be made and sold as a disposable device.

The system and apparatus of the present invention are believed to be as accurate or more accurate than any of the known patient-controlled drug delivery devices, all of which are substantially more expensive than the apparatus and system of the present invention and require dedication to an electrical power source, either plug-in or battery.

The system of the present invention includes a supply means for storing a beneficial agent and pump means for expressing the beneficial agent from the supply means. In the preferred embodiment, the pump means is a completely mechanical device. The supply means and pump means are preferably as provided by the Travenol Infusor, manufactured and sold by Travenol Laboratories, Inc. of Deerfield, Ill. and described for example in U.S.

Pat. No. 4,386,929 to Peery et al. entitled, "Elastomeric Bladder Assembly".

The system of the present invention further includes a dose reservoir downstream of the supply means for receiving a preselected quantity of beneficial agent, and control means actuated by the patient for expressing the dose volume of the beneficial agent or a fraction thereof from the dose reservoir and into the patient. Upstream Passageway means such as flexible plastic conduit connects the liquid supply having the beneficial agent therein with the dose reservoir. Downstream passageway means connect the dose reservoir with the patient access site such as at an intravenous catheter.

The apparatus of the present invention includes the dose reservoir and control means. The system of the present invention provides for a substantially constant flow rate of beneficial agent from the supply means to the dose reservoir, the flow rate being preset so as to prevent a toxic dose of beneficial agent from being delivered to the patient.

The control means includes a control switch actuated by the patient and operatively connected to valve means including a first mode closing the passageway means out of the dose reservoir to the patient and a second mode in which that passageway means is open. The control means includes biasing means which maintains the valve means in the closed mode until the biasing means is overcome by the actuation force provided by the patient on the control switch.

The control switch is further operatively connected to dose reservoir compression means for compressing the dose reservoir and expressing the beneficial agent out of the dose reservoir through the outlet thereof and into the patient. The apparatus of the present invention assures actuation of the valve means into the open mode before actuation of the compression means, thereby preventing a dangerously high pressure level in the dose reservoir.

In one embodiment of the invention, the dose reservoir comprises a flexible sheet sealed by means such as a pressure seal about its periphery against the back plate of the housing, thereby forming the dose reservoir therebetween. In a second embodiment of the invention, the dose reservoir is formed by means of two flexible sheets sealed together about their peripheries. In a third embodiment of the invention, an initially separate set that includes the dose reservoir and the upstream and downstream passageway means is provided. The set is installed into the apparatus housing. In the first and second embodiments, the entire apparatus may be treated as a disposable unit. In the third embodiment the housing may be treated as suitable for repeated use, with only the disposable set being replaced.

DETAILED DESCRIPTION OF PREFERRED EMBODIMENTS

The First Embodiment

Figures 1, 1A:
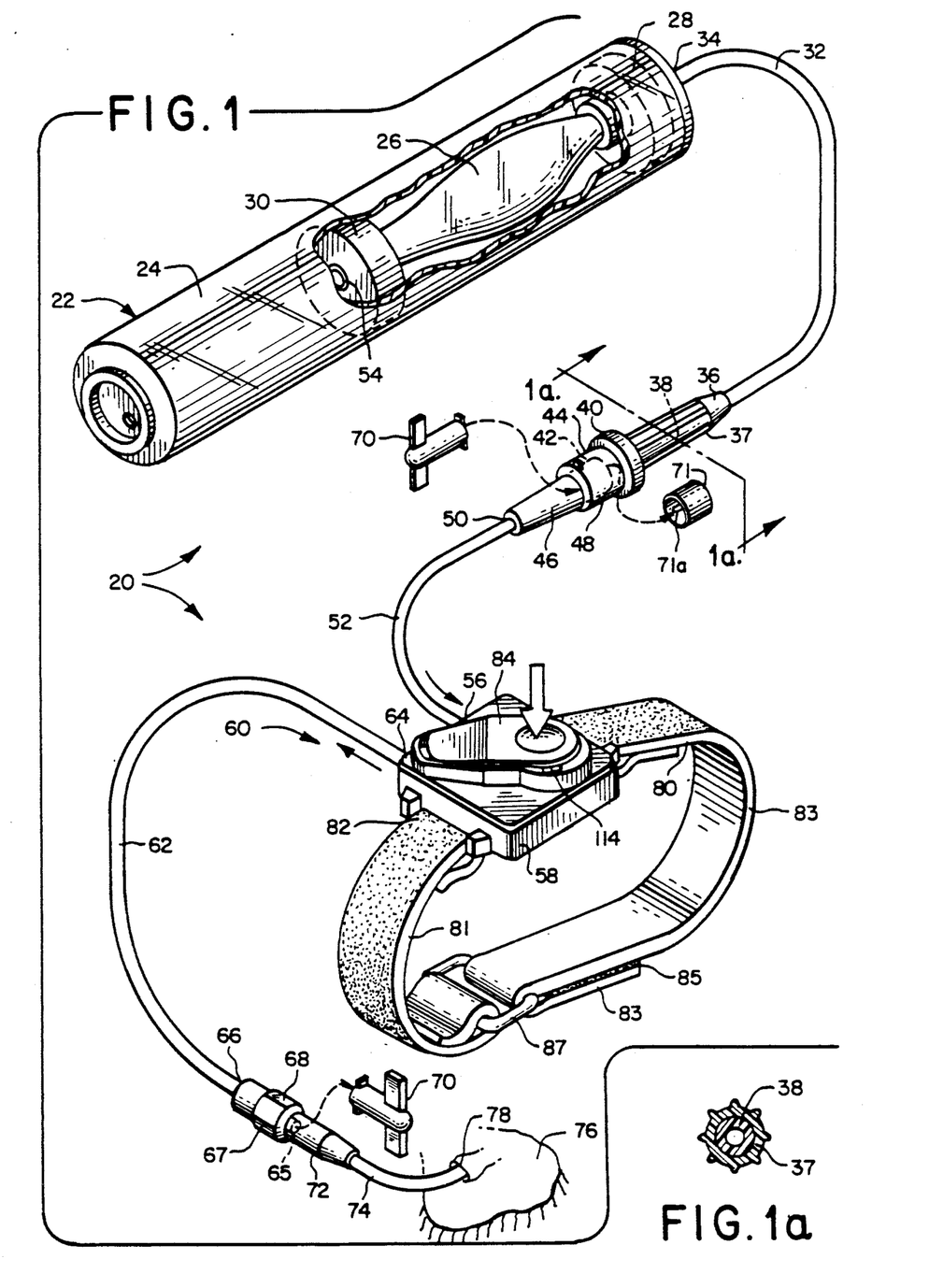
FIG. 1 is a perspective view of the system of the present invention.
FIG. 1a is a cross-sectional view taken at line 1a—1a of FIG. 1.
Figure 2:
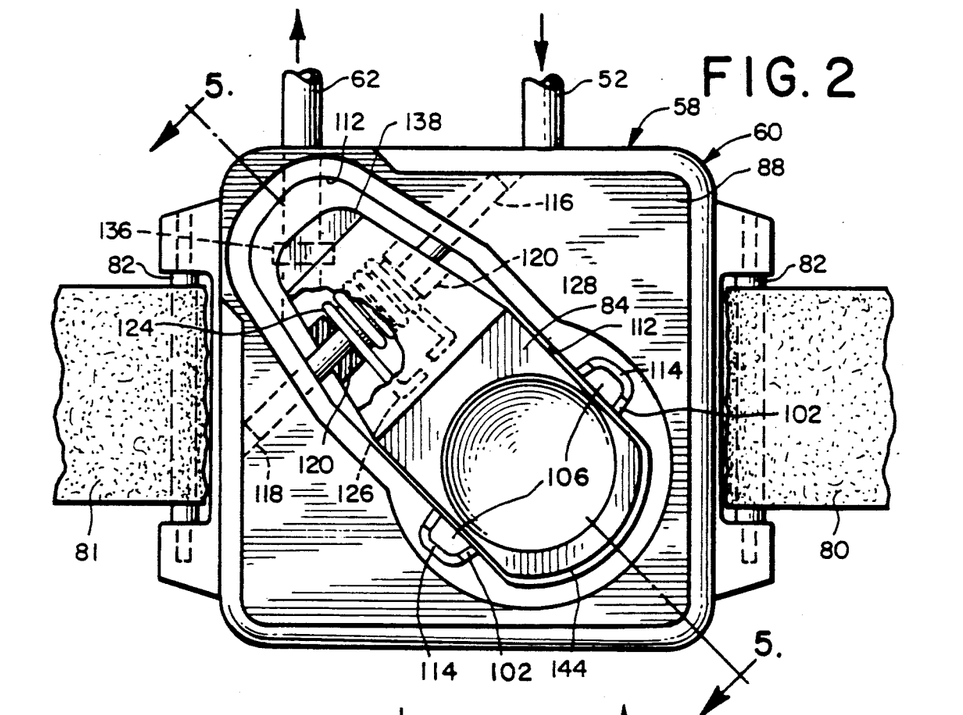
FIG. 2 is a top plan view of the apparatus of the present invention.
Figure 3:
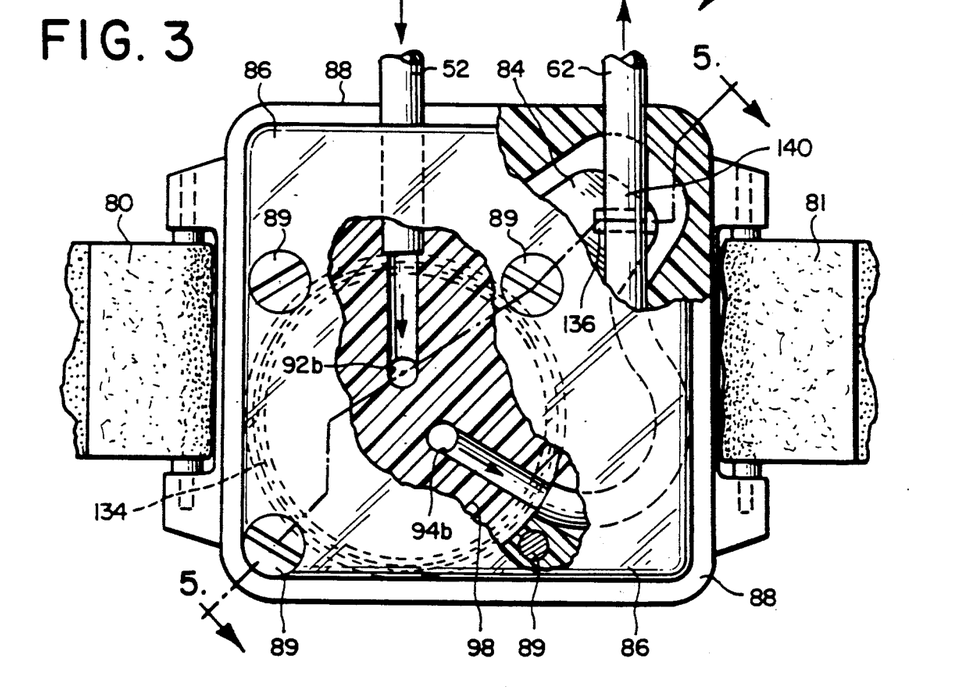
FIG. 3 is a bottom plan view of the apparatus of the present invention.

Referring to FIG. 1, there is illustrated the system 20 of the present invention. The system 20 includes an elastomeric bladder assembly 22 which in turn comprises both supply means and pump means. The elastomeric bladder assembly 22 includes a shell 24 in which is mounted an elastomeric bladder 26 secured at one end to a shell end cap 28 and at the other end to a floating piston 30 which moves along the length of the shell 24 as the bladder 26 is filled and emptied. The interior of the elastomeric bladder 26 communicates with the interior of bladder assembly tubing 32 connected at its proximal end 34 to the shell end cap 28. The distal end 36 of the bladder assembly tubing 32 includes capillary housing 37 containing a glass capillary flow restrictor 38, and a male Luer taper locking device 40. The male Luer taper locking device 40 includes the male Luer taper 42 and an outer internally threaded locking ring 44 for securing the locking device 42 to a female Luer taper 46 with external flanges 48 mounted at the proximal end 50 of the upstream apparatus conduit 52.

The elastomeric bladder assembly 22 is similar to that sold under the name Travenol ® Infusor by Travenol Laboratories of Deerfield, Ill., Product Code No. 2C1070, the principal differences being that the flow rate of the system 20 is set at a higher rate than that commercial product and the flow rate restrictor 38 is at the distal end 36 of the assembly tubing 32. In Product Code No. 2C1070 the flow restrictor is in the shell end cap. An elastomeric bladder assembly with a distal flow restrictor such as illustrated in FIG. 1 is shown in copending U.S. patent application Ser. No. 689,420 filed on Jan. 7, 1985, assigned to the assignee of the present invention. Although the system 20 will work with the flow restrictor 38 in either location, it is believed that the system 20 works best with the distal flow restrictor location illustrated in FIG. 1.

The elastomeric bladder 26 of the assembly 22 is self-pressurized; i.e., as a liquid such as a beneficial agent is injected through the injection site 54 of the assembly 22, the elastomeric bladder 26 expands. The elastomeric bladder 26 exerts a substantially constant pressure on its liquid contents throughout the volume range of the elastomeric bladder 26. The pressure from the bladder 26 on the liquid therein is about eight to ten PSI, although the pressure of the liquid after passing through the flow restrictor 38 is much lower, preferably just at or slightly higher than venous pressure.

The glass capillary flow restrictor 38 determines the rate of fluid flow out the male Luer taper 42, at a substantially constant flow rate. In the preferred embodiment of the invention, the elastomeric bladder assembly 22, with the flow restrictor 38, is manufactured to deliver liquid at a flow rate of approximately five mls per hour.

Figures 4, 4A:
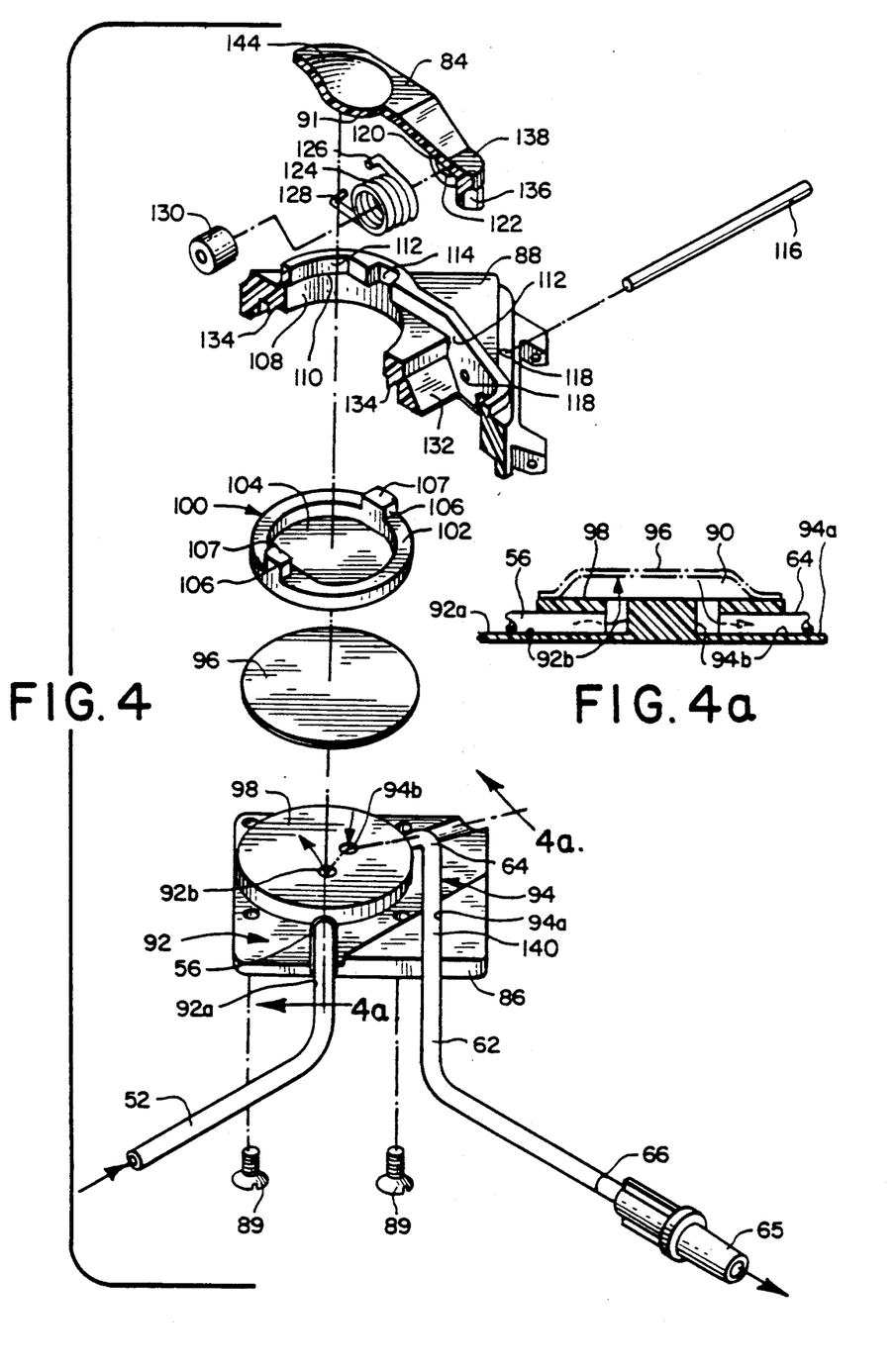
FIG. 4 is a partially cut-away, exploded view of the apparatus.
FIG. 4a is a fragmentary cross-sectional view taken at line 4a—4a of FIG. 4.

The apparatus 60 of the present invention includes upstream passageway means, which comprises the female Luer taper 46 and the upstream apparatus conduit 52 which is connected at its distal end 56 to the housing 58. The apparatus 60 includes downstream passageway means including downstream apparatus conduit 62 connected at its proximal end 64 to the housing 58 and including at its distal end 66 a male Luer taper locking device 68 which may be like the male Luer taper locking device 40 of the elastomeric bladder assembly 22, including a male Luer taper 65 and a locking ring 67. In FIG. 4 the locking ring 67 is not shown in order to illustrate the Luer taper 65. The upstream and downstream conduits 52, 62 may be made of polyvinyl chloride material.

The male Luer taper locking devices 40, 68 include removable pressure closures 70 to keep the fluid paths of the bladder assembly 22 and the apparatus 60 closed from the outside environment and maintain whatever necessary degree of sterility has been previously obtained in the fluid paths, until a closure is removed. The removable closures 70 are preferably like the closure sold by Travenol Laboratories, Inc. with its Travenol Infusor, Product Code No. 2C1070 and disclosed in U.S. patent application Ser. No. 420,981, filed Sept. 21, 1982. The pressure closures 70 prohibit the flow of liquid even when the bladder assembly 22 and the system 20 are stored for extended time periods such as up to two weeks after the bladder 26 is filled. The female Luer taper 46 includes a removable closure 71 of standard construction, including an internal closure male Luer taper 71a. The closures 70, 71 are typically removed by hospital personnel.

After the pharmacist fills the elastomeric bladder assembly 22, he or she connects the male Luer taper locking device 40 of the assembly 22 to the female Luer taper 46 of the apparatus 60. The pressure closure 70 on the male Luer taper locking device 68 prevents flow of the beneficial agent out of the apparatus 60 even if the control switch 84 is inadvertently activated before connection of the system 20 to the patient's injection site 78.

The male Luer taper locking device 68 may be secured to the catheter hub 72 of a catheter 74 such as an intravenous catheter. The catheter 74 pierces the patient's skin 76 at the patient injection site 78.

The housing 58 of the apparatus 60 may be worn in the same manner as a watch. In the preferred embodiment, the housing 58 includes wrist band portions 80, 81 which may be made of Velcro ® material to provide for infinite adjustment of the band 80, 81. The band portion 80 includes a pad segment 83, and a bristle segment 85. The band 80 is inserted through the clasp 87. The bristle segment 85 is then folded back to grasp the pad segment 83. The wrist band portions 80, 81 may be secured to the housing 58 in the same manner as a watch, the housing 58 including mounting pins 82 to which the wrist band portions 80, 81 are secured.

Referring now to FIGS. 2 through 8 and particularly FIGS. 2 through 4a, the housing 58 of the apparatus 60 includes a back plate 86 secured by plurality of screws 89 or other securement means to a casing 88. The back plate 86 may be optically transparent to permit a visual inspection of the interior of the housing 58.

A portion of the back plate 86 is a raised plateau 98 that forms one wall of the dose reservoir 90. A dose reservoir inlet 92 and a dose reservoir outlet 94 are formed within the back plate 86. Referring to FIG. 4, in the illustrated embodiment, the inlet 92 includes a channel portion 92a and a bore portion 92b communicating with the channel portion 92a and the interior of the dose reservoir 90. The upstream apparatus conduit 52 is secured by friction fit and also preferably by solvent bonding into the bore portion 92b. The conduit may be secured by solvent bonding to the channel portion 92a. The channel portion 92a serves as a track to trap the conduit in a fixed location when the back plate 86 is secured to the casing 88.

Similarly, the dose reservoir outlet 94 includes an outlet channel portion 94a and an outlet bore portion 92b communicating with both the interior of the dose reservoir 90 and with the outlet channel portion 94a. The downstream apparatus conduit 62 is secured to the outlet 94 in the same manner as the upstream conduit 52 is secured to the inlet 92.

A circular, flexible sheet 96 is placed on top of the raised plateau 98 of the back plate 86. The periphery of the circular flexible sheet 96 rests on the periphery of the raised plateau 98. The circular flexible sheet 96 may be made of polyisoprene rubber material for example.

The dose reservoir 90 is formed by utilizing pressure seal structure in the housing to press the flexible sheet 96 adjacent its periphery against the raised plateau 98, creating a liquid-tight seal between the sheet 96 and the plateau 98. More particularly, the casing 88 includes a downwardly extending annular rib 134 disposed below and outwardly of the guide bore 108, so that the annular rib 134 is directly above the periphery of the sheet 96 and the raised plateau 98. When the back plate 86 is secured to the casing 88 such as with the four screws 89 during manufacture, the periphery of the circular flexible sheet 96 is trapped between the annular rib 134 and the raised plateau.

The control means of the apparatus includes dose reservoir compression means which in the preferred embodiment of the invention includes a floating plate 100 that rests on top of the flexible sheet 96 and has a diameter less than the diameter of the raised plateau 98. The floating plate 100 includes an upper annular ridge 102 projecting from the top side 104 of the floating plate 100 at its periphery. The floating plate 100 further includes two volume indicator pegs 106 projecting from the upper annular ridge 102.

The casing 88 includes a guide bore 108. A casing ridge projects inwardly from the guide bore 108 at the top of the guide bore and acts as a stop 110 that is part of the dose compression means. The floating plate 100 travels in a direction perpendicular to the back plate 86, the stop 110 serving as an upper limit for the floating plate 100 when the upper annular ridge 102 thereof engages the stop 110.

The casing 88 defines an opening 112 for the control switch 84. Part of the opening 112 is directly above the guide bore 108 and the floating plate 100. The defined opening 112 of the casing 88 includes slots 114 in which the volume indicator pegs 106 of the floating plate 100 travel as the floating plate reaches its upper limit.

The control switch 84 is rotatably mounted upon a cylindrical pin 116 mounted in receiving sockets 118 within the casing 88. The control switch 84 includes two mounting flanges 120 each having a pin opening 122 through which the pin 116 extends.

The control switch 84 rotates within a narrow arc about the axis of the pin 116. A coil-type spring 124 is also mounted about the pin 116, between the mounting flanges 120. The pin extends through the inside of the coil-type spring 124. The spring 124 includes contact ends 126, 128. A spacer 130 is mounted on the pin between the coil-type spring 124 and the pin 116. The contact ends 126, 128 tend to move circumferentially relative to the axis of the pin 116 and the axis of the coil-type spring 124.

The contact end 126 contacts and urges against the underside 91 of the control switch 84. The contact end 128 contacts and urges against a shelf 132 in the casing 88. The coil-type spring 124 serves as the biasing means of the apparatus 60.

In the preferred embodiment, the control switch 84 also includes a blunt ended conduit occlusion bar 136 made integrally with the control switch and forming a single rigid part. The conduit occlusion bar 136 depends downwardly from the valve end 138 of the control switch 84. As described below, the conduit occlusion bar 136 acts with the flexible wall portion 140 of the downstream apparatus conduit 62 to form valve means for the apparatus 60. In the preferred embodiment the flexible wall portion 140 of the conduit 62 is a tubing segment of silicone material, although it is believed possible to make the flexible wall portion 140 of polyvinyl chloride material, just like the remainder of the downstream conduit 62. The silicone material segment is however easier to occlude than the polyvinyl chloride material.

OPERATION

Referring now to FIGS. 5 through 8, there is illustrated the operation of the apparatus 60, which when used in conjunction with a beneficial agent supply means and pump means such as the elastomeric bladder assembly 22, together form a unique, safe, and effective system 20 for the patient-controlled delivery of a beneficial agent such as an analgesic.

Figure 5:
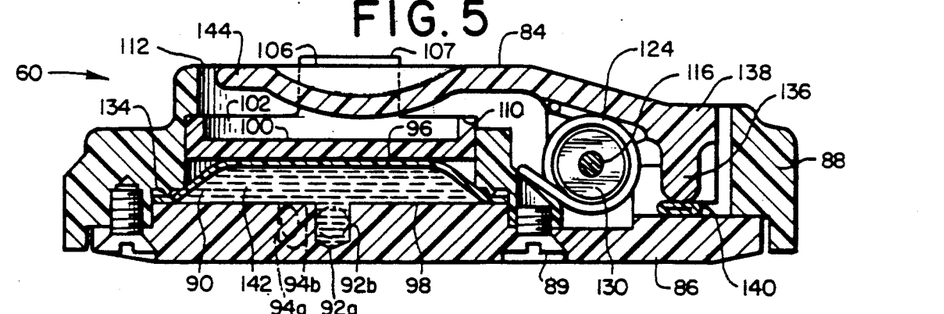
FIG. 5 is a cross-sectional view of the apparatus taken through line 5—5 of FIGS. 2 and 3, illustrating the dose reservoir in the filled state and the valve means in the closed mode.

Referring first to FIG. 5, there is shown the apparatus 60 after connection to the supply means and pump means. The dose reservoir 90 is filled with a beneficial agent 142 to its maximum volume, which in the preferred embodiment is 0.5 ml. Because of the small but steady flow provided by the pump means, the dose reservoir 90 has over time expanded to its maximum volume, the maximum volume being defined and limited by the floating plate 100 as limited by the stop 110. The spring 124 has biased the valve end 138 of the control switch 84, including the conduit occlusion bar 136, downwardly. Similarly, the spring 124 has biased the button end 144 of the control switch 84 upwardly, so that the button switch, although remaining within the defined opening 112 of the casing 88, is spaced from the floating plate 100. The flexible wall portion 140 of the downstream apparatus conduit 62 is disposed directly underneath the conduit occlusion bar 136. Indeed, the entire downstream apparatus conduit 62 may be flexible.

FIG. 5 illustrates the valve means in the closed mode of operation because the blunt-ended conduit occlusion bar 136 is biased against the flexible wall portion 140 of the downstream conduit 62, compressing the wall portion together to occlude the downstream apparatus conduit 62 and thus also the downstream passageway means.

In the state illustrated in FIG. 5, the top 107 of each volume indicator peg 106 now projects upwardly just slightly beyond the top of the casing 88. The indicator pegs 106 are intended to provide both visual and tactile notice to the patient that the dose reservoir 90 is now full. Because the top 107 of each peg 106 extends slightly above the top of the casing 88, the patient can tell when the dose reservoir 90 is full even in the dark, such as when in bed in the middle of the night. If desired the pegs 106 may be designed to not project this far. With such a construction the pegs could still provide visual notice of a full dose reservoir.

Another function of the volume indicator pegs 106 is that by moving within the slots 114, they help to maintain the floating plate 100 parallel to the raised plateau 98 during movement of the floating plate 100.

Figure 6:
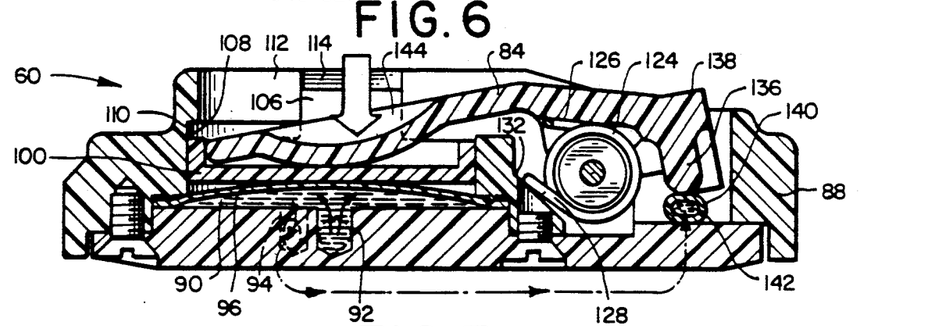
FIG. 6 is a cross-sectional view as in FIG. 5, illustrating the control switch as depressed by the patient, with the valve means in the open mode and the compression means compressing the dose reservoir.

FIG. 6 represents the apparatus 60 as it is being actuated by the patient. The patient pushes the button end 144 of the control switch 84, the button end 144 thereby contacting the floating plate 100 and depressing it downwardly out of engagement with the stop 110 and compressing the dose reservoir 90 by urging the flexible sheet 96 against the raised plateau 98, which is a portion of the back plate 86. However, it is important to the operation of the apparatus that before contact between the button end 144 and floating plate 100 is made, the biasing force provided by the spring 124 is overcome by the force of control switch actuation, lifting the valve end 138 and the conduit occlusion bar 136 out of engagement with the flexible wall portion 140 of the downstream conduit 62, placing the valve means in the open operating mode. Because the valve means opens before the dose reservoir 90 is compressed, the build-up of a dangerously high pressure within the dose reservoir is prevented, thus preventing rupture of the dose reservoir 90 and also preventing a dangerously high initial surge of pressure to the patient.

As the floating plate is urged downwardly by the control switch 84, the dose of beneficial agent 142 within the dose reservoir 90 is expressed out of the dose reservoir 90, through the outlet 94, downstream apparatus conduit 62 and the male Luer taper locking device 68 and then on through the catheter 74 and into the patient.

Figure 7:
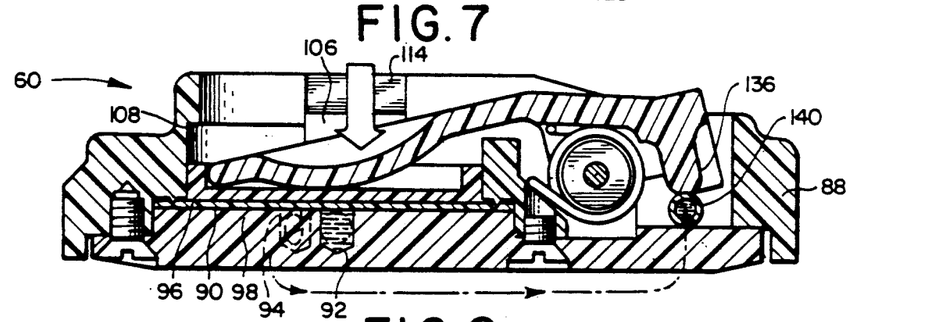
FIG. 7 is a cross-sectional view as in FIG. 5, illustrating the control switch as fully depressed by the patient, with the dose reservoir completely compressed.

FIG. 7 illustrates the apparatus 60 as still actuated by the patient depressing the control switch 84, with the dose reservoir 90 fully compressed so that the reservoir 90 is either empty or virtually empty, containing only a minute amount of beneficial agent. The valve means 136,140 remains in the open mode of operation as long as the patient holds down the button-end 144 of the control switch 84; however, during such time no additional fluid with beneficial agent 142 therein may enter the dose reservoir 90 because of the pressure applied by the floating plate 100. If a residual, minute amount of beneficial agent does remain within the dose reservoir 90, this may be accounted for during manufacture of the apparatus 60 so that the volume of the dose delivered upon patient actuation may be accurately determined.

Figure 8:
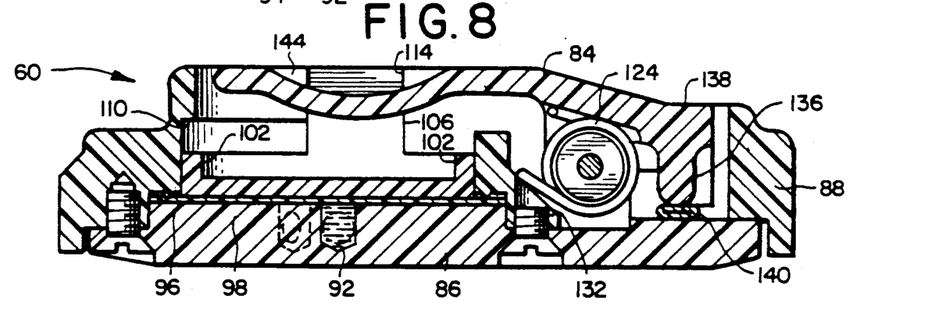
FIG. 8 is a cross-sectional view as in FIG. 5, immediately after patient release of the control switch, illustrating the valve means in the closed mode, with the dose reservoir not yet filled.

FIG. 8 illustrates the apparatus 60 soon after the patient actuation cycle represented by FIGS. 6 and 7 has been completed and the control switch 84 has been released. The flexible wall portion 140 of the downstream apparatus conduit 62 is now once again occluded by the blunt-ended conduit occlusion bar 136. The valve means is thus in the closed mode of operation. In addition to closing the valve, the biasing spring 124 has also returned the button end 144 of the control switch 84 to its unactuated, upper position. The dose reservoir 90 is empty or virtually empty, the flexible sheet 96 of the dose reservoir remaining adjacent the back plate 86. The floating plate 100 rests on the circular flexible sheet 96. However, unlike the state represented in FIG. 7, the floating plate 100 can be urged upwardly by the pressure of liquid entering the dose reservoir 90.

With time, liquid from the elastomeric bladder assembly 22 will be pumped into the dose reservoir 90 through the inlet 92, thereby urging the flexible sheet 96 and thus also the floating plate 100 away from the raised plateau 98 of tee back plate 86. This expansion of the dose reservoir 96 will continue until the upper annular ridge 102 of the floating plate 100 engages the stop 110, thereby limiting the maximum volume of the dose reservoir 90 and returning the apparatus 60 to the state illustrated by FIG. 5.

In the preferred embodiment of the invention, the 0.5 ml dose reservoir 90 is filled in six minutes, although other time periods and dosage reservoir volumes are certainly possible, given the speed of the pumping means and the desired drug dose. However, the system 20, preset with a particular pumping rate and dose reservoir volume when manufactured, may be used for a variety of dosage requirements by adjusting the concentration of the beneficial agent in the liquid, e.g., sterile water, to be delivered to the apparatus 60 and the patient.

With the apparatus as described above, a patient who has just completed actuation of the control switch 84 and has thereby received a dose of beneficial agent 142, may receive another full dose of beneficial agent in six minutes. The patient can wait longer than six minutes if desired; similarily, the patient must wait at least six minutes to receive another full dose.

However, if the patient actuates the control switch 84 sometime within the six-minute fill period of the dose reservoir 90, the patient will receive a fraction of a dose, the dose fraction value being substantially equal to the fraction of the fill time period that has elapsed. Thus, as an example, if the patient actuates the control switch 84 two minutes after a previous actuation of the control switch, the patient will receive one-third of a dose volume, given the six-minute fill period of the present example. The system 20 of the present invention permits this consistent calculation of dose delivery because the dose reservoir 90 is filled at a rate which is linear over time; i.e., the dose reservoir fill rate is substantially constant over any part of the fill period cycle.

This feature is important because it assures that no matter how often the patient actuates the control switch 84, he or she will never receive a toxic quantity of the beneficial agent. The patient will never receive more than a single dose of beneficial agent 142 during the fill period immediately following a previous actuation of the control switch 84. In the present example the fill period is six minutes.

The apparatus 60 and system 20 of the invention provide a solution to patient controlled delivery of a beneficial agent in a manner that permits no setting of any variables (and thus prevents any calculation error) by the patient or hospital personnel after the system 20 leaves the hospital pharmacy. The single calculation that must be made is the proper concentration of the beneficial agent. Standard conversion tables provided by the manufacturer can assist the hospital pharmacist in providing the correct dosage concentration.

THE SECOND AND THIRD EMBODIMENTS

Figure 9:
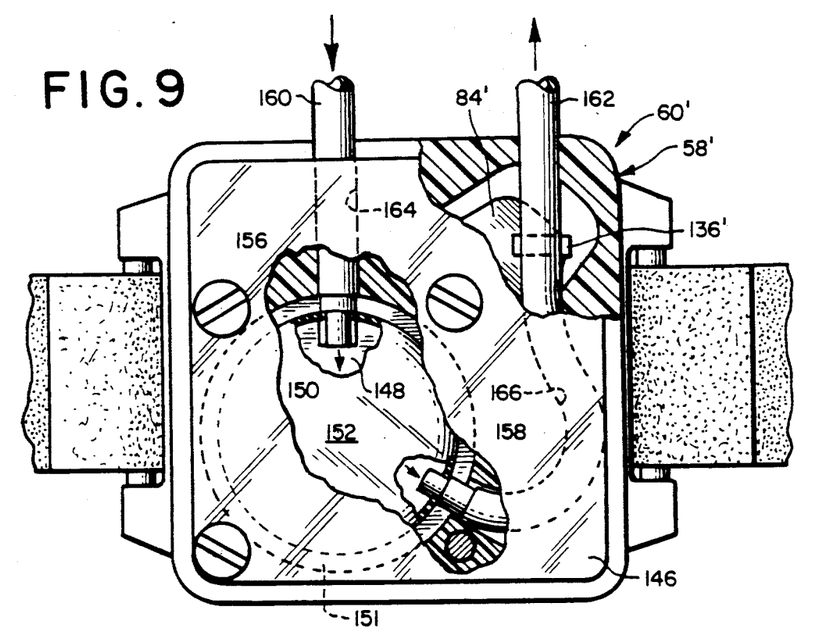
FIG. 9 is a bottom plan view of second and third embodiments of the apparatus of the invention.
Figure 10:
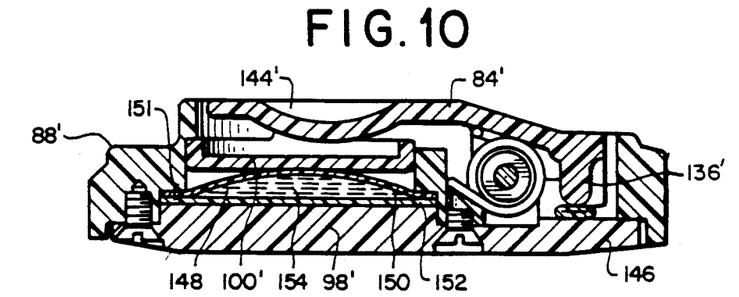
FIG. 10 is a cross-sectional view of the apparatus of FIG. 9.

Referring now to FIGS. 9 and 10, there is disclosed a second embodiment of the present invention.

Here, the apparatus 60' includes a housing 58' made from a casing 88' and a back plate 146. As with the first embodiment, a control switch 84' also includes a conduit occlusion bar 136'. The control switch 84' is used to depress the floating plate 100' and the dose reservoir 148.

Although identical in operation to the apparatus 60, the apparatus 60' has a dose reservoir 148 that is made as a preformed unit such as by two flexible sheets 150, 152 of polyvinyl chloride material sealed at their peripheries 151 to form a chamber 154. The flexible sheets 150, 152 are sidewalls closing the chamber except for an inlet 156 and an outlet 158. At least a portion of one of the flexible sheets 150, 152 is flexible enough to be pressed against the opposite sheet by the button end 144' of the control switch 84' and the floating plate 100'. As shown in FIGS. 9 and 10, the dose reservoir 148 is a pillow-like structure wherein both sheets 150, 152 are flexible.

Because of the preformed dose reservoir 148, the back plate 146 and the casing 88' do not require the seal structure present in the first embodiment for sealing the flexible sheet 96 to the back plate 86. The annular rib 134 is no longer necessary. The back plate 146 no longer includes the inlet bore 92b and the outlet bore 94b. Instead, the inlet and outlet 156, 158 may be formed by sealing the upstream apparatus conduit 160 and the downstream apparatus conduit 162 directly between the flexible sheets 150, 152, by means of solvent bonding for example. The back plate 146 may include entrance and exit channels 164, 166 respectively to ensure that upstream and downstream conduit 160, 162 remain in a fixed location within the housing 58'.

In the second embodiment, the apparatus 60' is manufactured with the upstream and downstream conduits 160, 162 and the dose reservoir 148 within the housing 58'. Thus, the external appearance of the apparatus 60' could be the same as the appearance of the apparatus 60.

Alternatively, a third embodiment of the apparatus of the invention would be identical to the apparatus 60', except that the housing 58' is delivered to the pharmacist separately from the upstream and downstream conduits 160, 162 and the dose reservoir 148. In such a third embodiment, an apparatus set 168 such as illustrated in FIG. 11 may be sold separately to be installed by hospital personnel within the housing 58', so that after installation the apparatus 60' with the set 168 therein is as illustrated in FIGS. 9 and 10.

Figure 11:
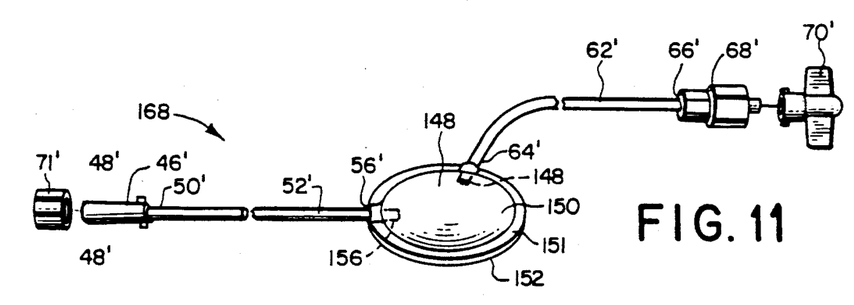
FIG. 11 is a perspective view of a set which may be used with the apparatus of FIG. 9 in the third embodiment.

As illustrated in FIG. 11, the apparatus set 168 includes a removable closure 71' closing the end of the female Luer adapter 46' having external flanges 48' thereon. The female Luer taper 46' is connected to upstream apparatus conduit 52' at the proximal end 50' thereof. The distal end 56' of the upstream conduit 52' is sealed between the two flexible sheets 150, 152 of the dose reservoir 148, forming an inlet 156 thereto. The sheets 150, 152 are sealed at their peripheries 151.

The dose reservoir 148 further includes an outlet 158 formed by the securement of the proximal end 64' of the downstream apparatus conduit 62' between the flexible sheets 150, 152. The distal end 66' of the downstream conduit 62' is secured to a male Luer taper locking device 68' for securement to the catheter hub of a catheter for access into the patient's body such as at the venous system. A removable pressure closure 70' closes the male Luer taper locking device 68'.

While the several embodiments and features have been described in detail herein and shown in the accompanying drawings, it will be evident that various further modifications are possible without departing from the scope of the invention.

That which is claimed is:

1. A system for the patient-controlled delivery of a beneficial agent, comprising:
   (a) supply means for storing the beneficial agent;
   (b) conduit means for transporting the beneficial agent from the supply means to a dose reservoir;
   (c) pump means for expressing the beneficial agent out of the supply means through the conduit means and into a dose reservoir at a controlled rate;
   (d) a dose reservoir for receiving a dose of beneficial agent from the supply means;
   (e) control means operative by the patient for selectively expressing the beneficial agent out of said dose reservoir, through an outlet thereof, in at least one of discrete dose volumes or fractional dose volumes, as selected by the patient; and
   (f) excess dose prevention means for supplying the beneficial agent to the dose reservoir at a predetermined flow rate that fills the volume of the dose reservoir substantially linearly with time up to the discrete dose volume;
   (g) wherein said system is patient-wearable and permits the patient to be ambulatory.

2. The system in accordance with claim 1, wherein said supply means and said pump means comprise an expandable, elastomeric, self-pressurized bladder for storing and pumping the beneficial agent.

3. An apparatus for the patient-controlled delivery of a beneficial agent comprising:
   (a) a dose reservoir for receiving and storing a dose of beneficial agent;
   (b) an inlet to said dose reservoir, for receiving the beneficial agent under pressure;
   (c) an outlet to said dose reservoir, through which beneficial agent in said dose reservoir exits said dose reservoir;
   (d) downstream passageway means having a proximal end in communication with said outlet; and
   (e) control means operative by the patient for selectively expressing the beneficial agent out of said dose reservoir, through said outlet, said control means comprising
     (i) valve means having a closed mode of operation whereby said downstream passageway means is closed and an open mode of operation whereby said downstream passageway means is open, permitting flow of the beneficial agent therethrough;
     (ii) biasing means for biasing said valve means in said closed operating mode;
     (iii) dose reservoir compression means for compressing said dose reservoir; and
     (iv) a control switch operatively connected to said valve means, said biasing means, and said compression means, such that the force of actuation of said control switch by the patient overcomes said biasing means and places said valve means in said open mode of operation, the force of actuation of said control switch also causing said control switch to operatively engage said compression means to reduce the volume of said dose reservoir and express the beneficial agent out of said dose reservoir and said outlet while said valve means is in said open mode of operation;
   (f) wherein said apparatus may be worn by the patient and permits the patient to be ambulatory.

4. The apparatus in accordance with claim 3, wherein said dose reservoir comprises an upper volume limit substantially equal to a dose volume.

5. The apparatus in accordance with claim 3, including downstream conduit secured at one end to said outlet and having a distal end adaptable for securement to an intravenous catheter.

6. The apparatus in accordance with claim 3, wherein said control means may be repeatedly actuated by the patient, said control means permitting the delivery of multiple doses of the beneficial agent to the patient at a controlled delivery rate.

7. The apparatus in accordance with claim 3, further comprising a housing for said dose reservoir and said control means.

8. The apparatus in accordance with claim 3, wherein said control switch overcomes said biasing means and urges said valve means into said open mode before said control switch actuates said compression means, so that said compression means does not urge the beneficial agent out of said drug reservoir until after said valve means is in said open mode of operation.

9. The apparatus in accordance with claim 3, wherein said biasing means comprises a spring.

10. The apparatus in accordance with claim 3, wherein said downstream passageway means includes a downstream apparatus conduit having a flexible wall portion and wherein said valve means comprises a conduit occlusion bar which in said closed mode of operation is urged by said biasing means against said flexible wall portion, compressing said wall together to occlude said conduit.

11. The apparatus in accordance with claim 10, wherein said conduit occlusion bar and said control switch form an integral, rigid part.

12. The apparatus in accordance with claim 3, wherein said dose reservoir compression means comprises:
   (a) a floating plate;
   (b) a stop engaged by said floating plate upon expansion of said dose reservoir to a certain, predetermined maximum volume, said stop and said floating plate together preventing further expansion of said dose reservoir;
   (c) whereby patient-actuation of said control switch engages said floating plate and, when said drug reservoir is filled to its maximum volume, also disengages said floating plate from said stop.

13. The apparatus in accordance with claim 12, further comprising:
   (a) at least one volume indicator peg extending from said floating plate on said control switch side thereof; and
   (b) a housing for said dose reservoir and said control means, said housing defining an opening for said control switch, wherein said peg is visible through said opening when said dose reservoir is full.

14. The apparatus in accordance with claim 13, wherein a portion of said peg is external of said housing when said dose reservoir is full.

15. The apparatus in accordance with claim 13, said defined opening defining a slot for each peg wherein said slot guides the travel of said floating plate to maintain said floating plate parallel to said back plate.

16. The apparatus in accordance with claim 3, further comprising a housing for said dose reservoir and said control means.

17. The apparatus in accordance with claim 3, wherein:
(a) said dose reservoir has one wall defined by said housing and further includes a flexible sheet;
(b) said dose reservoir further comprising pressure seal structure in said housing for pressing said flexible sheet adjacent its periphery against said reservoir-defining wall of said housing, creating a liquid-tight seal therebetween.

18. The apparatus in accordance with claim 3, wherein said dose reservoir comprises chamber-defining sidewalls forming a chamber closed except for said inlet and said outlet, wherein at least a portion of one of said sidewalls may be pressed against the opposite sidewall by said compression means.

19. The apparatus in accordance with claim 18 wherein said apparatus permits said dose reservoir to be removed from said housing and replaced with another one of said dose reservoirs.

20. The apparatus in accordance with claim 3, further comprising upstream passageway means having a distal end in communication with said inlet.

21. The apparatus in accordance with claim 3, further comprising said control means for permitting delivery of fractional doses of the beneficial agent to the patient.

22. The apparatus in accordance with claim 3, further comprising said control means for preventing delivery of a quantity of beneficial agent to the patient in excess of the dose volume within a preselected time period.

23. An apparatus for patient controlled delivery of an agent comprising:
a dose reservoir in fluid communications with an outlet and an inlet, the dose reservoir having a maximum capacity which represents the discrete dose limit to be administered to the patient;
excessive dose prevention means for supplying a predetermined flow rate of the agent to the dose reservoir such that after a predetermined fill time the dose reservoir is filled to maximum capacity;
valve means having a closed mode of operation whereby the outlet is closed and an open mode of operation whereby the outlet is open, permitting flow of the beneficial agent therethrough;
biasing means for biasing the valve means in the closed operating mode;
dose reservoir compression means for compressing the dose reservoir; and
a control switch operatively connected to the valve means, the biasing means, and the dose reservoir means such that the force of actuation of the control switch overcomes the biasing means and places the valve means in the open mode of operation, the force of actuation of the control switch also causing the control switch to operatively engage the compression means to reduce the volume of the dose reservoir and express the beneficial agent out of the dose reservoir and the outlet while the valve means is in the open mode of operation;
whereby operation of the valve means prior to the fill time results in an amount of agent less than the discrete dose maximum being administered to the patient.

24. The apparatus of claim 23 wherein the predetermined flow rate causes the volume of agent in the dose reservoir to increase substantially linearly with time up to the maximum capacity of the dose reservoir.

25. The apparatus of claim 23, further including a supply means for storing the beneficial agent and pump means in fluid communications with the supply means and the inlet for expressing the agent from the supply means to the dose reservoir.

26. The apparatus of claim 25 wherein the supply means and the pump means comprise on expandable, elastomeric, self pressurized bladder for storing and pumping the agent.

27. The apparatus of claim 25, wherein the supply means and the pump means comprises a source of pressurized fluid for storing and pumping the agent.

28. The apparatus of claim 23, further including a downstream conduit secured at one end to the outlet and having a distal end adaptable for securement into an intravenous catheter.

29. The apparatus of claim 23, wherein the dose reservoir is removable.

30. The apparatus of claim 23, further including housing containing the apparatus and wrist band portions connected to the housing so that the apparatus can be worn in the manner of a watch.

* * * * *